(12) United States Patent
Rufer et al.

(10) Patent No.: US 8,476,868 B2
(45) Date of Patent: Jul. 2, 2013

(54) AMBULATORY INFUSION DEVICE WITH VARIABLE ENERGY STORAGE TESTING AND METHOD FOR TESTING AN ENERGY STORAGE

(75) Inventors: Thomas Rufer, Ostermundigen (CH); Reto Aeschlimann, Aefligen (CH)

(73) Assignee: Roche Diagnostics International AG, Rotkreuz (CH)

( * ) Notice: Subject to any disclaimer, the term of this patent is extended or adjusted under 35 U.S.C. 154(b) by 376 days.

(21) Appl. No.: 12/977,392

(22) Filed: Dec. 23, 2010

(65) Prior Publication Data

US 2011/0279123 A1 Nov. 17, 2011

(30) Foreign Application Priority Data

Dec. 28, 2009 (EP) .................................. 09016038

(51) Int. Cl.
*H01M 10/44* (2006.01)
*H01M 10/46* (2006.01)

(52) U.S. Cl.
USPC ........................................................ 320/114

(58) Field of Classification Search
USPC .................. 320/107, 114, 115, 166; 324/426, 324/427, 433; 607/5, 75
See application file for complete search history.

(56) References Cited

U.S. PATENT DOCUMENTS

| | | | |
|---|---|---|---|
| 4,345,603 A | | 8/1982 | Schulman |
| 5,140,269 A | * | 8/1992 | Champlin ..................... 324/433 |
| 5,904,707 A | | 5/1999 | Ochs et al. |
| 2001/0056561 A1 | * | 12/2001 | Rub ............................... 714/746 |
| 2002/0171428 A1 | * | 11/2002 | Bertness ........................ 324/426 |
| 2006/0282227 A1 | * | 12/2006 | Bertness ........................... 702/63 |
| 2008/0015644 A1 | | 1/2008 | Julian et al. |
| 2008/0269724 A1 | | 10/2008 | Sarkinen et al. |
| 2009/0209945 A1 | | 8/2009 | Lobl et al. |
| 2011/0160665 A1 | * | 6/2011 | Rufer et al. .................... 604/131 |

FOREIGN PATENT DOCUMENTS

| | | |
|---|---|---|
| EP | 1 619 512 A2 | 1/2006 |
| WO | 2008/129549 A1 | 10/2008 |

OTHER PUBLICATIONS

Extended European Search Report, Appln. No. EP09016038.3, Aug. 11, 2010, 5 pages.

* cited by examiner

*Primary Examiner* — Edward Tso
(74) *Attorney, Agent, or Firm* — Dinsmore & Shohl LLP

(57) ABSTRACT

Included are embodiments of an ambulatory infusion device. Some embodiments include an energy storage for storing electrical energy utilized for powering the ambulatory infusion device. The energy storage may serve as a primary power source of the ambulatory infusion device. Also included is a dosing unit with an electrically powered actuator and an electronic controller, where the electronic controller controls operation of the electrically powered actuator. Some embodiments also include a testing unit for testing the energy storage. The testing unit may be configured to repeatedly carry out a test during operation of the ambulatory infusion device. Additionally, the test may include determining a control variable, the control variable being indicative of a capability of the energy storage for further powering the ambulatory infusion device.

15 Claims, 11 Drawing Sheets

AMBULATORY INFUSION DEVICE WITH VARIABLE ENERGY STORAGE TESTING AND METHOD FOR TESTING AN ENERGY STORAGE

TECHNICAL FIELD

The present disclosure is related to ambulatory infusion devices including a testing unit for testing the energy storage capabilities of the devices and to methods for testing the energy storage capabilities of such devices.

BACKGROUND

External ambulatory infusion devices for the infusion of a liquid drug over an extended time period may be utilized for a number of therapies. In particular, such devices form the basis for a therapy of Diabetes Mellitus by CSII (Continuous Subcutaneous Insulin Infusion. Besides diabetes therapy, those devices may be used for a number of additional therapies, such as cancer treatment or pain therapy, without requiring substantial modification.

Such devices are typically powered by one or more electrical energy storages. In the following description, the energy storage is assumed to be a rechargeable or non-rechargeable battery. It may, however, also be another kind of electrical energy storage, such as a high-energy capacitor or a fuel cell.

As described herein, a simplified battery model is used to aid: the energy storage is considered as a non-ideal battery, which includes an ideal battery. More specifically, the non-ideal battery may include an ideal DC voltage supply, having an off-circuit-voltage, in series with an internal resistor having an internal resistance. The off-circuit voltage is the voltage that can be measured between the battery terminals when no current is drawn from the battery. In contrast, the terminal voltage is the voltage that can be measured at the battery terminals under normal operational conditions. When current is drawn from the battery, it is generally smaller as compared to the off-circuit voltage because of a voltage drop over the internal resistor. The voltage drop is defined according to Ohm's law by the internal resistance and the current that is drawn. The terminal voltage equals the off-circuit voltage if no current is drawn. This is the case, for example, if the voltage is measured with a voltage measurement unit of substantially infinite input resistance.

When an energy storage component such as a battery is being used, neither its off-circuit voltage nor its internal resistance is constant over time. The off-circuit voltage decreases and the internal resistance increases. Both effects reduce the terminal voltage if current is drawn. These effects are illustrated in FIG. 9, showing an exemplary off-circuit voltage $U_0$ curve 600 and the corresponding internal resistance $R_i$ curve 605 as measured over the usage time of an exemplary battery.

In many existing devices, a battery may be connected to a test load, such that the battery is stressed with a defined testing stress and the corresponding terminal voltage is measured in order to ensure that the device does not abruptly terminate operation due to a depleted battery. The measured terminal voltage is compared to at least one alerting voltage threshold and the user of the device is alerted if the voltage is below the threshold. Testing is typically carried out repeatedly with a time interval of some minutes. If the infusion device is, for example, an insulin pump that is designed for pulsed insulin administration of a small amount of insulin every few minutes, the testing may be carried out prior to, during and/or after each administration.

Testing is accompanied by the drawback that each test is associated with some power consumption by the test load, thus reducing the remaining usage time of the energy storage. Furthermore, it has been found that some batteries show a defect or anomaly which results in the terminal voltage dropping from a high level at which no alert would be generated to a very low level that is not sufficient for operating the device, with a steep drop of the terminal voltage within a short time. The device may accordingly terminate operation without alerting the user. Since the user is, in case of this event, not aware of the terminated infusion of the drug or substance, severe adverse effects may result.

SUMMARY

Included are embodiments of an ambulatory infusion device. Some embodiments include an energy storage for storing electrical energy utilized for powering the ambulatory infusion device. The energy storage may serve as a primary power source of the ambulatory infusion device. Also included is a dosing unit with an electrically powered actuator and an electronic controller, where the electronic controller controls operation of the electrically powered actuator. Some embodiments also include a testing unit for testing the energy storage. The testing unit may be configured to repeatedly carry out a test during operation of the ambulatory infusion device. Additionally, the test may include determining a control variable, the control variable being indicative of a capability of the energy storage for further powering the ambulatory infusion device.

Also included are embodiments of a method. Some embodiments include repeatedly carrying out tests during operation of the ambulatory infusion device. At least one of the tests may include determination of a control variable, where the control variable is indicative of a capability of the electrical energy storage for further powering the ambulatory infusion device. Additionally, some embodiments include varying the testing in dependence of the control variable.

BRIEF DESCRIPTION

In the following, exemplary embodiments of the disclosure are described with reference to the following figures:

FIG. 1 shows an outside view of a device in accordance with the present disclosure.

FIG. 2 schematically shows an electrical diagram of a device in accordance with the present disclosure.

Figure 5:
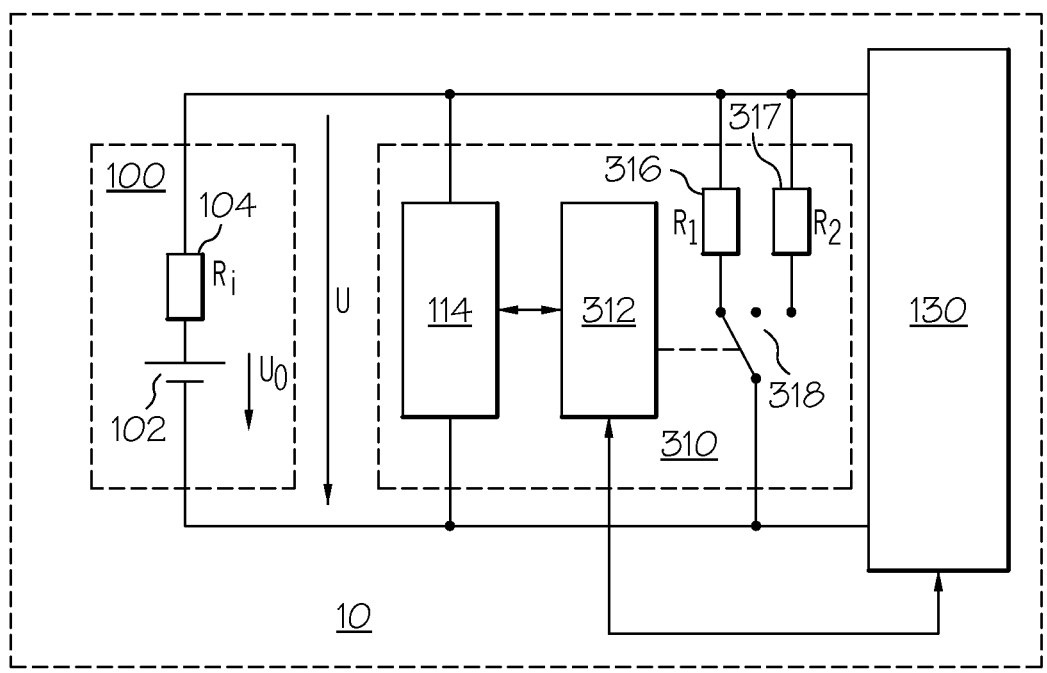

FIG. 5 schematically shows an electrical diagram of a device in accordance with the present disclosure.

Figure 6:
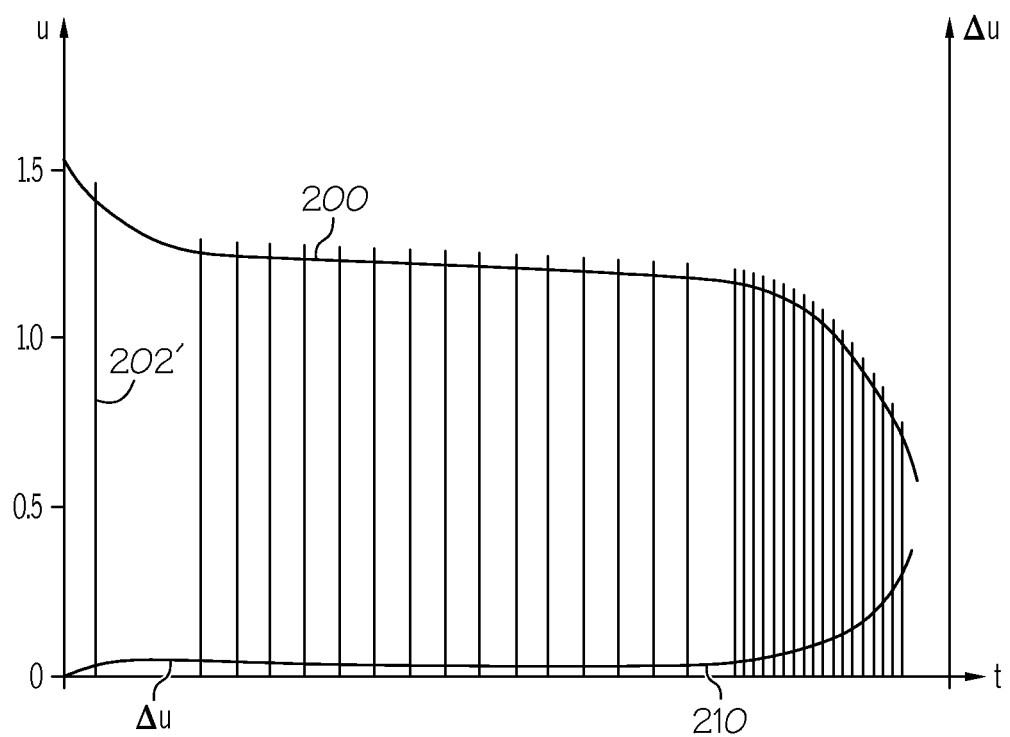

FIG. 6 shows a battery voltage of a device according FIG. 5 and a difference voltage as a function of time along with the times for testing the battery.

Figure 7:
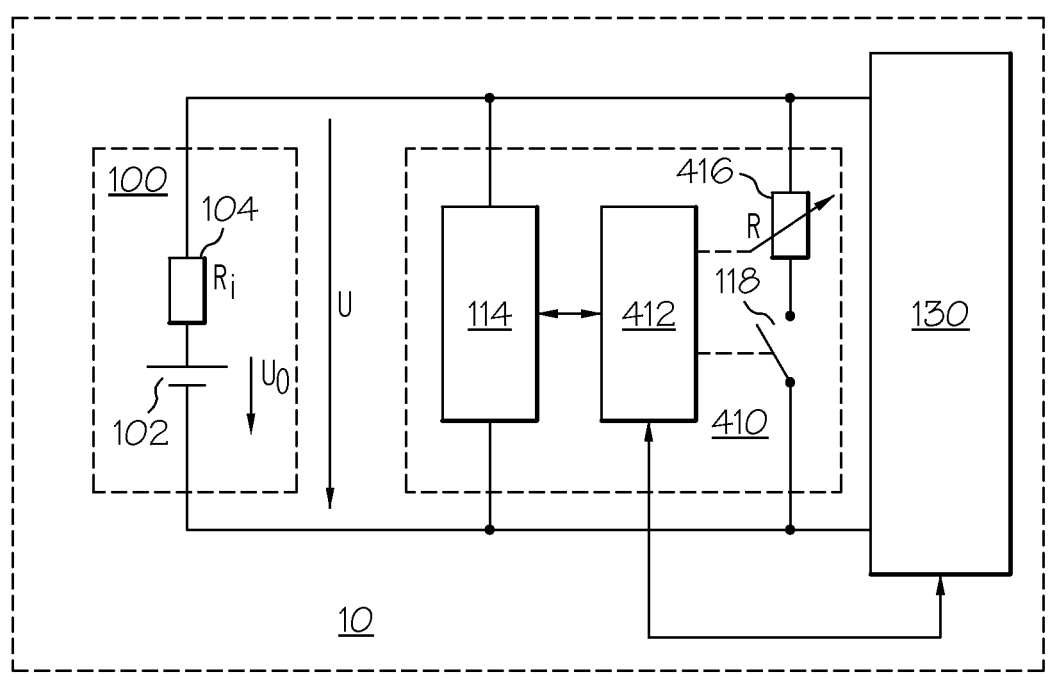

FIG. 7 schematically shows an electrical diagram of a still further device in accordance with the present disclosure.

Figure 8:
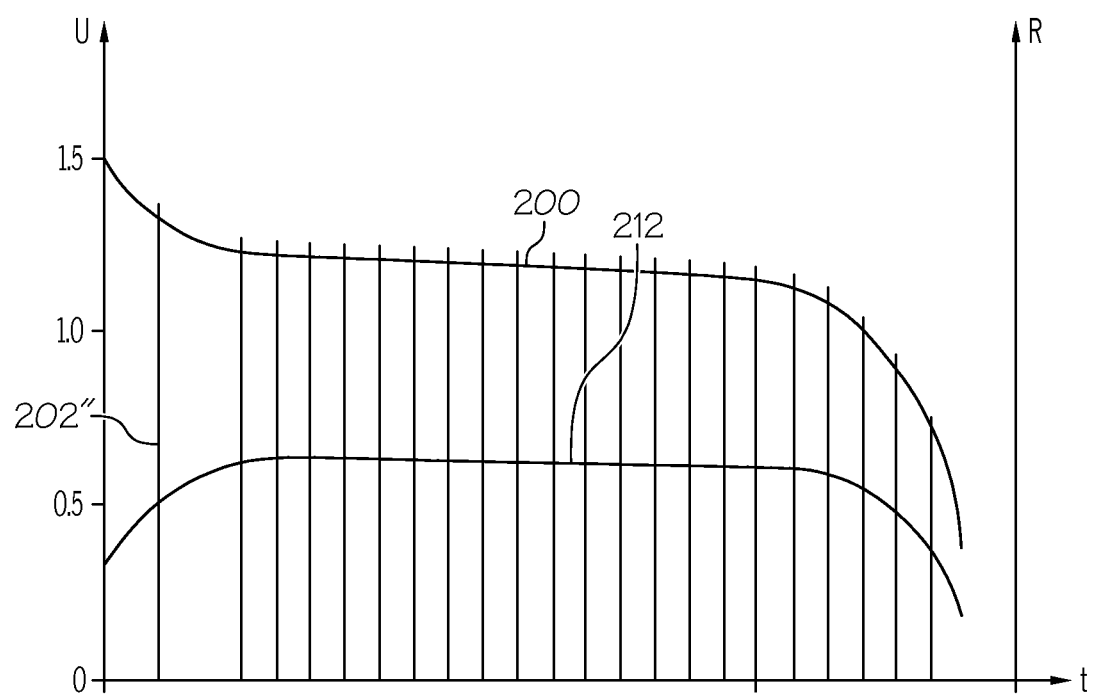

FIG. 8 shows a battery voltage of a device according FIG. 7 and a test load resistance as a function of time along with the times for testing the battery.

Figure 9:
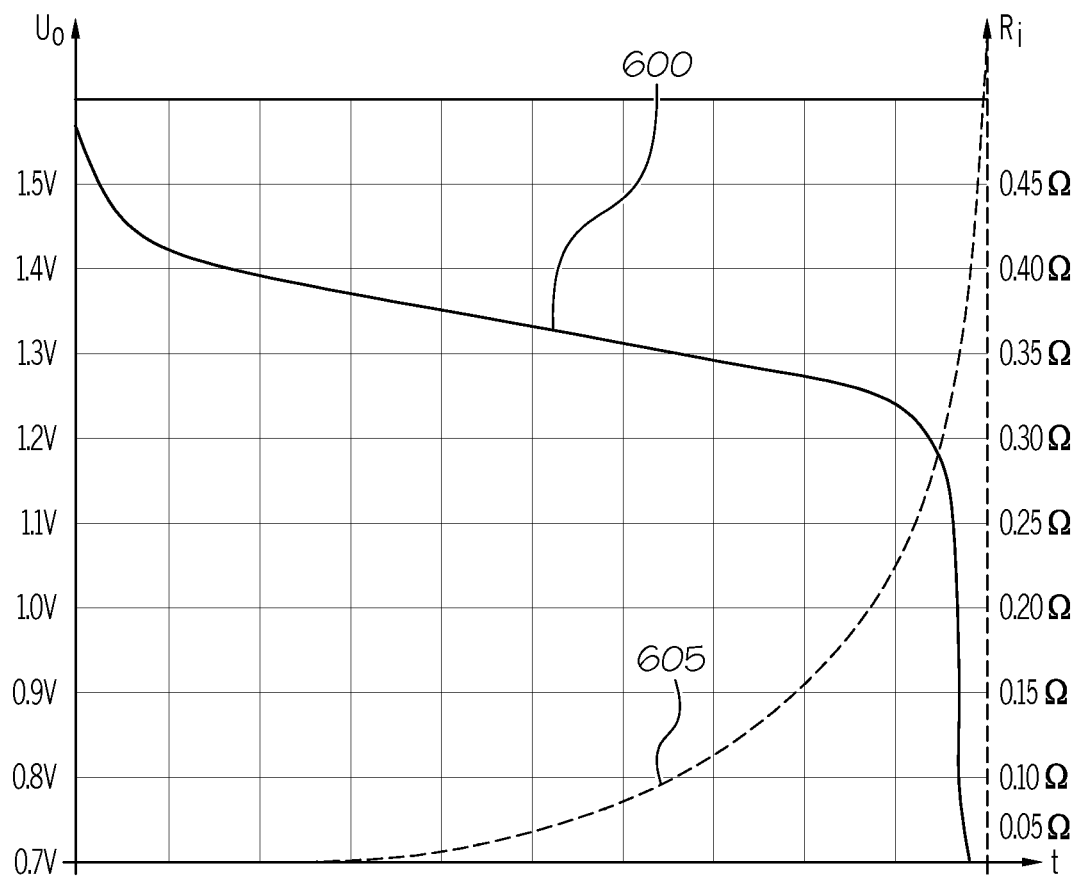

FIG. 9 shows an exemplary off-circuit voltage curve and a corresponding internal resistance curve of a battery.

Figure 10:
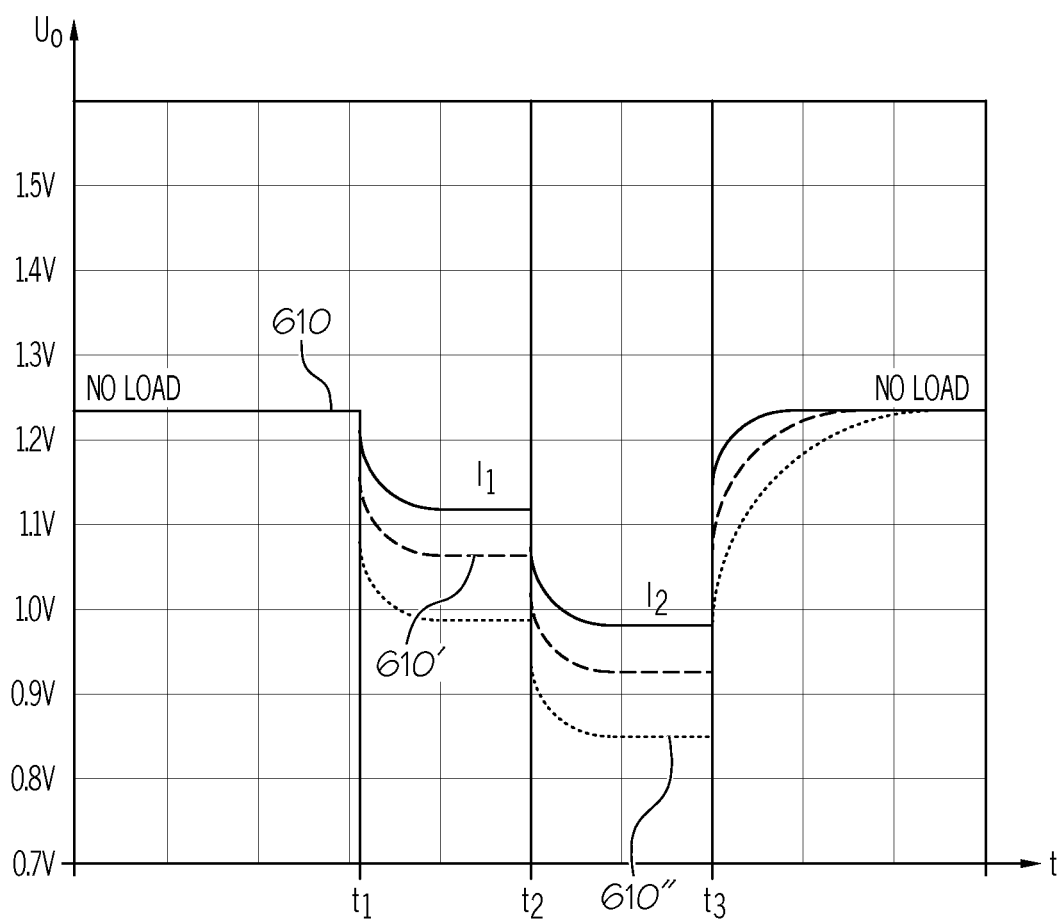

FIG. 10 shows an exemplary embodiment of the terminal voltage as function of time of batteries in different depletion states when consecutively coupled to two different test loads.

Figure 11:
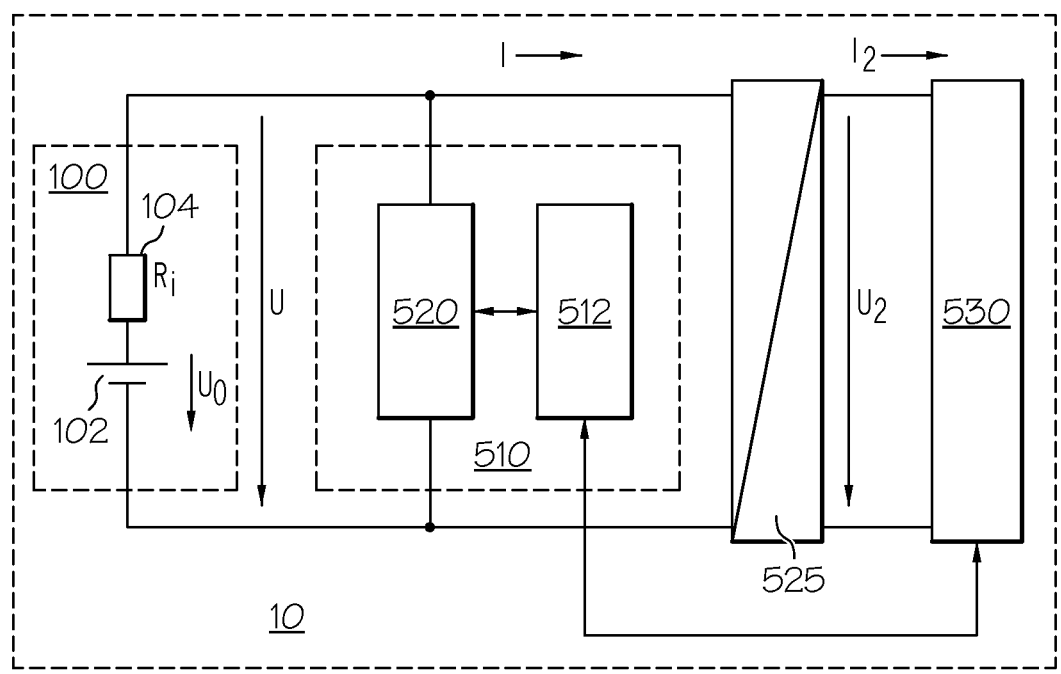

FIG. 11 shows an electrical diagram of a still further device in accordance with the present disclosure.

Figure 12:
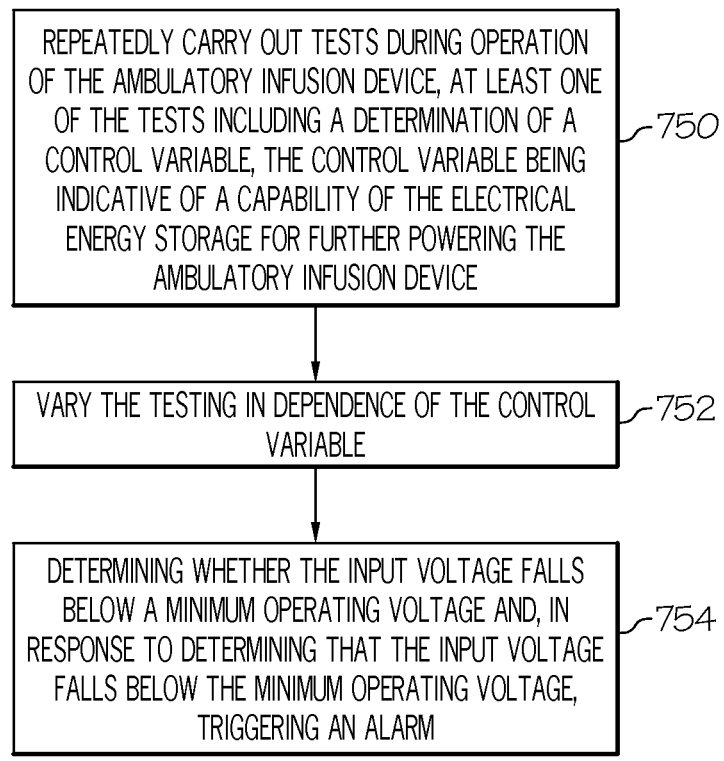

FIG. 12 shows a flowchart illustrating an embodiment of a process, in accordance with the present disclosure.

DETAILED DESCRIPTION

Embodiments of the present disclosure provide improved ambulatory infusion devices and methods for testing an energy storage component of such devices which avoid or reduce the drawbacks as described above. This is met based on the insight that an improvement can be achieved by variable testing over the usage time of the energy storage in dependence of the capability of the energy storage for further powering the device. In accordance with the disclosure, the power consumption due to extensive testing can be largely avoided at times when testing is less critical while still carrying out sufficient testing where required, and thus avoiding or reducing the drawbacks of current devices as discussed above.

As will become more readily apparent, the phrase "capability for powering the device" is used in the sense of a qualitative measure of the state of the energy storage. The capability is assumed to be maximum for a fresh energy storage component and is reduced over the usage time of the energy storage as the energy storage is depleted. For a non-ideal battery, the decreasing off-current voltage or terminal voltage as well as the increasing internal resistance over time reduce the capability of the battery for powering the device. The energy storage is assumed to be capable for powering the device if sufficient current can be drawn form at a sufficiently high terminal voltage such that the device operates as intended. In a first aspect, the present disclosure is directed towards an ambulatory infusion device, including an energy storage for storing electrical energy required for powering the device, a dosing unit with an electrically powered actuator and an electronic controller, the controller controlling operation of the actuator, a testing unit for testing the energy storage, the testing unit being designed to repeatedly carry out a test during operation of the device, the test including determining a control variable, the control variable being indicative of a capability of the energy storage for further powering the device. The energy storage serves as primary power source of the ambulatory device and is successively depleted during application. In accordance with embodiments of the present disclosure, the testing unit may be configured to vary the testing of the energy storage in dependence of the control variable.

As will be described in more detail below, the testing may be varied by varying the time interval between consecutive tests, and thus, the testing frequency, and/or by varying the testing stress that is exerted on the battery in each test. Varying the testing stress is associated with varying the current, power, and/or the energy that is drawn from the energy storage in a test. In accordance with the disclosure, the testing is varied such that the testing frequency and/or the testing stress are increased over the usage time of the energy storage.

The dosing unit may include a spindle drive as currently used in many ambulatory infusion devices, a peristaltic pump head, a micro-membrane or a micro-piston pump, or the like. The actuator may include a motor, an electromagnet, piezoelectric elements, or the like. The controller typically includes one or multiple microcontrollers and additional circuitry such as power circuitry for driving the actuator, memory and safety circuitry. The device may include further units such as a user interface and communication interfaces for the communication with external devices. These further units may be integral with or, fully or partly, separate from the dosing unit.

The phrase "powering the device" is used in the sense of providing power such that the device operates and in particular infuses drug or a substance via the dosing unit as intended. The phrase "operation of the device" refers to the device operating in mode where it carries out repeated or continuous drug administrations. An insulin pump as used for CSII is in such an operational mode substantially permanently and typically administers an insulin pump every few minutes. The operation also includes the device operation between the administrations and typical further activities such as retracting a typically present spindle of the dosing unit when replacing a drug cartridge, powering a display backlight, providing alarms or alerts to the user or exchanging data with further devices.

The term "control variable" refers to a variable that is indicative for the capability of the energy storage for powering the device in the above-given meaning as well as to a variable that is derived from one or multiple of such variables. As will be discussed below in more detail, a terminal voltage, and/or an internal resistance of the energy storage or a variable derived from those may especially serve as a control variables in some embodiments.

The testing unit may therefore comprise a voltage measurement unit for measuring the terminal voltage of the energy storage and/or a resistance or impedance measurement unit for measuring the internal resistance of the energy storage. Exemplary embodiments for those measurement units are discussed below in more detail. A measured terminal voltage may also be substantially identical to the off-circuit voltage if measured by a voltage measurement unit of substantially infinite impedance and if no or negligible further current is drawn from the device. In this case, the phrase "off-circuit voltage" may be used for clarity reasons.

Instead of or in addition to the terminal voltage or the internal resistance as such, their first or second time derivative may serve as control variable. The testing unit may therefore be designed to determine a time derivative. In some embodiments, the testing unit includes a test load and a test includes temporarily coupling the test load to the energy storage and determining the resulting terminal voltage. Such a test load may be designed as at least one dedicated Ohmic resistor. It may, however, also be given by any other source of resistance that consumes power when connected to the energy storage and that can be powered without affecting the infusion, such as a display backlight.

When a load such as an Ohmic resistor is coupled to a battery, the terminal voltage shows a step response in the form of a downwards step in dependence of the internal resistance (see FIG. 10 as discussed below in the context of an exemplary embodiment). The test loads are favorably coupled to the energy storage for a time interval that is sufficiently long for the downwards step to be completed. For a typical battery, this time interval is in the range of some milliseconds. Coupling the test load to energy storage for a longer time interval consumes additional energy and typically without corresponding benefit.

In some embodiments including a test load, the test load is designed based on a maximum current and/or a maximum power drawn by the device during operation. The test load may especially be designed such that the testing current and/or testing power matches the maximum current and/or the maximum power drawn by the device during operation. In this context, the term "operation" refers to the normal device operation in contrast to energy storage tests.

Designing the test load in this way assures that the energy storage is tested under the worst case condition with respect to current or power consumption. Besides the actuator of the dosing unit, a considerable current and/or power may be drawn by indicators, such as acoustic and/or tactile indicators, a display backlight and wireless communication interfaces that may be present in the device.

As long as the terminal voltage stays in a range which is sufficient for operating the device while the test load is connected to the energy storage, it is also sufficient for general device operation. Such a design is especially suited if only one test load with a fixed test load resistance is present. As will be discussed below in the context of exemplary embodiments, two or more test loads may be present and may be coupled alternatively to the energy storage. In a further embodiment, a test load having a variable test load resistance is present.

Instead of the maximum current or power, the test load may draw another defined reference current and/or power. Drawing a current and/or power that is smaller than the maximum current and/or power may be sufficient if a theoretically possible maximum current and/or power is sufficiently unlikely to occur. On the other hand, the test load may be designed to draw a higher current and/or power for safety reasons and may, e.g., draw the maximum current and/or power plus an additional amount serving as a safety factor.

Measurements of the terminal voltage under load conditions may be taken with the test load being connected to the battery or shortly after disconnecting the test load, before the typically occurring recovery of the terminal voltage to the off-circuit voltage.

In some embodiments, the testing unit is designed to vary the testing by reducing a testing interval for carrying out consecutive tests as a change of the control variable indicates a decreasing capability of the energy storage for further powering the device. Reducing the testing interval is equivalent to increasing the testing frequency as reciprocal of the testing interval.

While some testing of the energy storage may be generally be performed also for an energy storage of full or nearly full capability, such as a fresh battery, very extensive testing is not necessary and only reduces the lifetime of the energy storage without benefit. For an energy storage approaching the end of its usage time, in contrast, more testing is favorable because of the rapid decrease of the off-current voltage and the increase of the internal resistance (see FIG. 9 and discussion above). The end of the usage time is a time where the energy storage is depleted to a degree where it is not further capable of securely powering the device. While there is no general upper limit for the testing interval, it should generally be sufficiently small to detect the points in time where the voltage starts considerably decreasing and/or the internal resistance starts considerably increasing because of the energy storage approaching the end of its usage time or because of a defect.

In some embodiments, which include varying the testing interval for consecutive tests, the testing unit is configured to reduce the testing interval and increase upon a decreasing terminal voltage and/or upon an increasing internal resistance of the energy storage. This type of embodiment will be discussed in more detail below in the context of exemplary embodiments.

Similarly, in some embodiments including a test load, the testing unit is configured to vary the testing by reducing the test load resistance as a change of the control variable indicates a decreasing capability of the energy storage for further powering the device. Reducing the test load resistance is associated with increasing the current that is drawn from the battery, and, thus, the testing stress that is exerted on the energy storage.

For a non-ideal battery as discussed above, the terminal voltage decreases with the current that is drawn from the battery because of an increasing voltage drop over the internal resistor. The terminal voltage further increases with increasing internal resistance. Reducing the test load resistance therefore has the effect that the terminal voltage shows an increasing downwards step when the test load is connected to the energy storage. In other words, decreasing the test load resistance results in the testing stress for the battery being increased.

In some embodiments including varying a test load resistance, the testing unit is configured to reduce the test load resistance upon a decreasing terminal voltage and/or upon an increasing internal resistance. This type of embodiment will be discussed in more detail below in the context of exemplary embodiments. In some embodiments, the testing unit is designed to trigger an alert upon a test indicating a lack of capability of the energy storage for further powering the device.

In embodiments involving coupling a test load to the energy storage and determining the terminal voltage, the energy storage is typically capable of powering the device if the terminal voltage with the test load being coupled to the energy storage does not fall below a minimum operating voltage of the device. For considering the energy consumption in the time period after a test and until the next following test is carried out, an alerting threshold voltage at which an alert is triggered should be selected somewhat higher as compared to the minimum operating voltage. The alerting threshold voltage may be determined experimentally and/or by calculation.

In embodiments where the testing unit is designed to determine the internal resistance of the energy storage as will be described below, a further approach may be used. With $U_0$ being the off-circuit voltage, $R_i$ being a measured internal resistance and $I_{ref}$ being a given reference current, e.g., the maximum current drawn by the device during operation, the energy storage is considered as being capable of powering the device if the condition $$U_0 - R_i * I_{ref} \geq U_{min} \qquad (1)$$

is fulfilled, wherein $U_{min}$ is the minimum operating voltage of the device. An alert is favorably generated at an alerting threshold voltage above the minimum operating voltage as discussed above.

Determining the internal resistance of the energy storage can be carried out with the current drawn from the energy storage being comparatively small as compared to the maximum current drawn by the device. Therefore, this type of embodiment involves particularly small energy consumption for testing. This kind of embodiment will be described in more detail in the context of a method in accordance with the present disclosure as well as in the context of exemplary embodiments.

In some embodiments, the device is powered, at least in part, via a voltage converter. For example, a motor serving as actuator in the dosing unit as well as some microcontrollers require a supply voltage that may be higher as compared to the battery voltage. A DC/DC voltage converter is provided in those embodiments for stepping-up and stabilizing the battery voltage. In those embodiments, the testing unit may be configured to trigger an alert upon a test indicating an input voltage of the voltage converter falling below a minimum operating voltage of the voltage converter.

According to a further aspect, the present disclosure is directed towards a method for testing an electrical energy storage of an ambulatory infusion device. Embodiments of the method include repeatedly carrying out tests during operation of the device, a test including determining a control variable, the control variable being indicative of a capability of the energy storage for further powering the device. In accordance with the disclosure, embodiments of the method further include varying the testing in dependence of the control variable.

In some embodiments, the tests are carried out at points in time where the device draws a defined and favorably small or negligible amount of further current and/or power from the energy storage in order not to overload the energy storage and to ensure reproducible testing conditions. For an insulin pump which is designed for quasi-continuous pulsed insulin administration, this condition is typically fulfilled prior to or some time after an administration.

In some embodiments, the method includes varying the testing by reducing a testing interval for carrying out consecutive tests as a change of the control variable indicates a decreasing capability of the energy storage for further powering the device. In still some embodiments, a test includes connecting a test load to the energy storage, the test load having a test load resistance, and the method further includes varying the testing by reducing the test load resistance as a change of the control variable indicates a decreasing capability of the energy storage for further powering the device.

The internal resistance of the energy storage may be determined by consecutively coupling the energy storage to two different test loads having test load resistances $R_1$ and $R_2$, respectively, and measuring the corresponding terminal voltages $U_1$ and $U_2$. From the voltage measurements and the resistances, the internal resistance, as well as the off-circuit voltage may be calculated by applying Ohm's law. The accuracy of the calculation increases with an increasing difference $\Delta R = |R_1 - R_2|$. In those embodiments, a test comprises varying the test load resistance.

Alternative to the internal resistance itself, the difference voltage $|U_1 - U_2|$ may serve as measure for the internal resistance and/or as control variable because it is correlated with the internal resistance and can be determined with less complicated hardware and/or less computational effort as compared to the internal resistance.

In some embodiments, the method includes determining a terminal voltage of the energy storage, and/or an internal resistance of the energy storage, or a variable derived from the terminal voltage and/or the internal resistance. The determined variable may especially serve as control variable for varying the testing. In still some embodiments including varying a testing interval for carrying out consecutive tests, the method includes decreasing the testing interval upon a decreasing terminal voltage and/or upon an increasing internal resistance.

In some embodiments including varying a test load resistance, the method includes reducing the test load resistance with the control variable indicating a decreasing capability of the energy storage for further powering the device. In some embodiments, the method includes triggering an alert upon a test indicating a lack of capability of the energy storage for further powering the device. In some embodiments, the method is carried out on a medical device which is powered, at least in part, via a voltage converter as discussed above. In those embodiments, the method may include triggering an alert upon a test indicating the input voltage of the voltage converter falling below a minimum operating voltage of the voltage converter.

Method steps that are disclosed in conjunction with structural units such as devices may be used for detailing method claims which are based on other portions of the description. In the same manner structural elements that are disclosed in conjunction with methods may be used for detailing structural claims.

Figure 1:
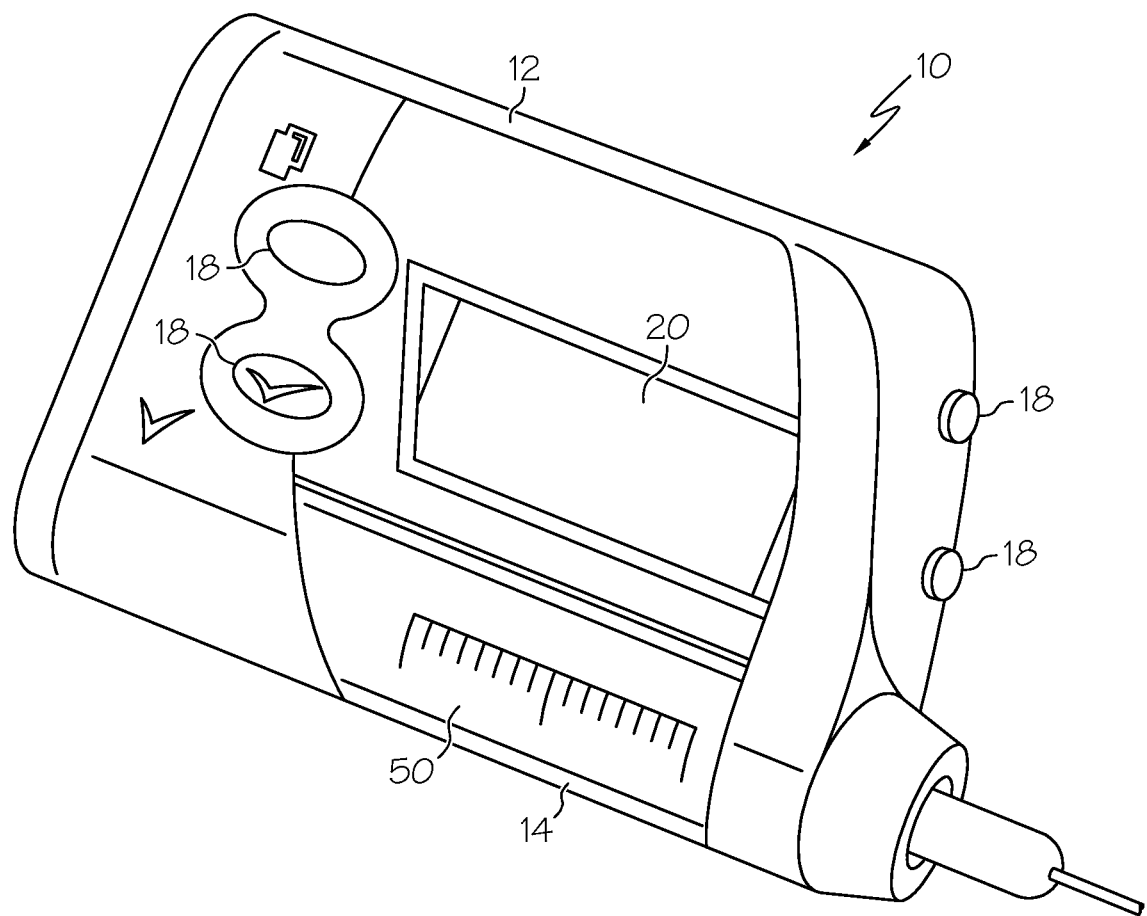

Referring now to the drawings, FIG. 1 shows an outside view of an exemplary ambulatory infusion device, such as the device 10 in accordance with the present disclosure such as used for CSII therapy of diabetes mellitus. The infusion device 10 has a housing 12 that includes a cartridge compartment 14 with a transparent window. The cartridge compartment 14 is designed to receive a cylindrical cartridge, such as the cartridge 50 of, for example, 3 ml or 300 I.U. (International Units) of insulin as maximum filling volume. From the cartridge 50, insulin is infused by displacing a cartridge plunger in a controlled way via a dosing unit with a motor-operated spindle drive. The displacement of the spindle and the overall operation of the device are controlled by an electronic controller. The device 10 further includes an input unit 18 in form of pushbuttons as well as a display 20. Further elements such as safety circuitry as well as data interfaces for remote controlling purposes and/or general data exchange purposes may additionally be present.

The device 10 further includes an electrical energy storage component in the form of a replaceable battery (not visible in FIG. 1), which may or may not be rechargeable. In some embodiments, however, the battery may not be replaceable and/or may be made by a high energy capacitor.

It should be understood that the general design shown in FIG. 1 is meant only to be exemplary. Several other designs and architectures for such devises may be utilized and/or modified in accordance with the present disclosure.

Figure 2:
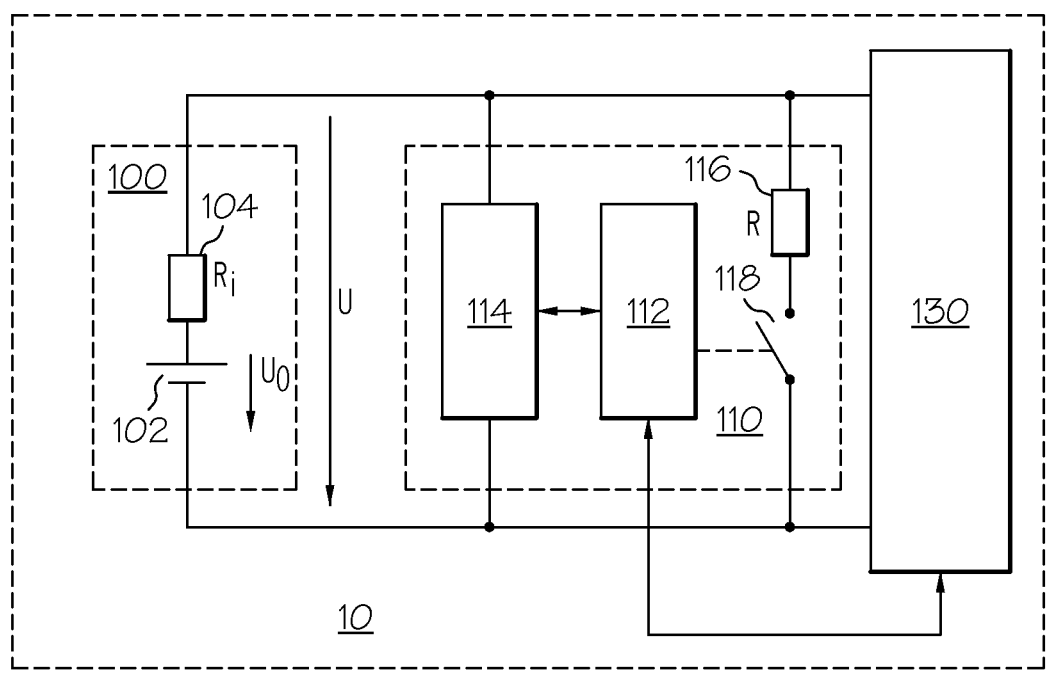

FIG. 2 shows a schematic electrical diagram of the device 10. The electrical energy storage of the device 10 is a non-ideal battery, such as battery 100 which can be modeled by an ideal battery 102 having an off-circuit voltage $U_0$ in series with an internal resistor 104 of resistance $R_i$ as described above. In an exemplary device, the battery 100 may have a nominal voltage of 1.5V and may be, for example, a standard AA or AAA cell. Other battery types having other nominal voltages may be used as well.

The device 10 further includes a testing unit 110. The testing unit 110 includes a test load in the form of a resistor 116, which can be selectively coupled to the terminals of the battery 100 via an electronically controlled switch, such as the switch 118. The test load resistance R of the resistor 116 is such that the current drawn from the battery 100 with the resistor 116 being coupled to the battery 100 approximately corresponds to the maximum current that occurs during normal operation of the device. In this way, the battery 100 is maximally stressed by the resistor 116, thus reflecting the "worst-case" situation. For a device as shown in FIG. 2, the resistance R of the resistor 116 is typically in a range from $10\,\Omega \ldots 20\,\Omega$. The switch 118 is closed for some milliseconds during each test. The switch 118 is schematically shown as a standard switch but may be realized as a semiconductor switch, using, a field effect transistor (FET) as a voltage-controlled switching element, for example.

The testing unit 110 further includes a measurement unit 114, which is in this example shown as voltage measurement unit coupled to the terminals of the battery 100, thus measuring the terminal voltage U as the control variable. The measurement unit 114 has a substantially infinite input resistance that is especially much larger as compared to the test load resistance R such that the measurement unit 114 does not significantly influence the voltage measurement.

Both the switch 118 and the measurement unit 114 are activated and controlled via a control unit 112 which also controls the overall operation of the testing unit 110. The results of the voltage measurements are further evaluated by the control unit 112.

Further circuitry of the device 10 is shown as combined in general circuitry 130. The general circuitry 130 includes in particular at least one microcontroller for controlling and supervising the device operation as well as a clock module which activates the testing unit 110 in given test intervals, thus triggering a test of the battery 100. The general circuitry 130 further includes the actuator of the dosing unit as well as an alerting unit. The alerting unit may include a display and at least one of the following: an acoustical and a tactile indicator, such as a pager vibrator.

It will be understood that while FIG. 2 shows the testing unit 110 as separate from the general circuitry 130, this is for illustrative purposes only. In practice, the testing unit 110 may be combined with the general circuitry 130 fully or in part in any desired or favorable way. In particular, the control unit 112 and the measurement unit 114 may be included in a microcontroller or the like which also serves further purposes. The measurement unit 114 may for example be based on an Analogue-to-Digital-Converter, which is present in many existing microcontrollers.

Figure 3:
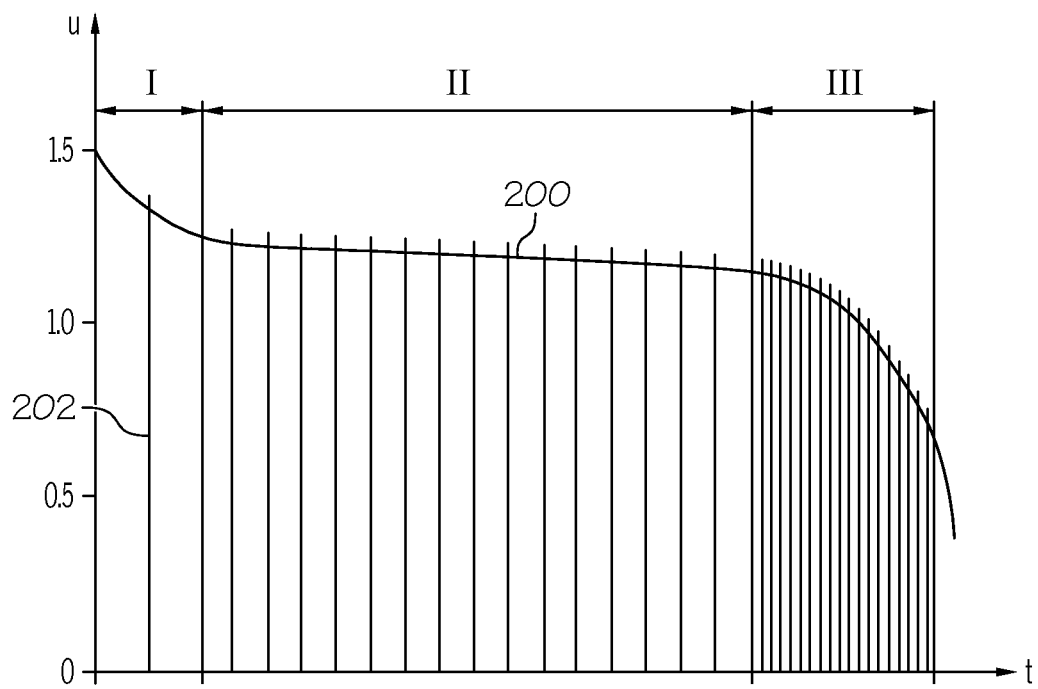
FIG. 3 shows a battery voltage of a device according FIG. 2 as a function of time along with the times for testing the battery.

FIG. 3 shows a typical curve 200 of the terminal voltage U of the battery 100 as a function of time t. The points in time where the battery 100 is tested are indicated by vertical lines 202. At those testing points in time, the voltage curve 200 shows the sampled terminal voltage U with the resistor 116 being connected to the battery 100. Between the testing points in time, the curve 200 is given by an interpolation of the sampled voltages. The whole usage time of a battery, and thus, the time span, which is shown in FIG. 3, is typically in the range of some weeks, depending on the device design, the battery type and the use habits of the device user. While the curve 200 holds qualitatively true for typical rechargeable as well as non-rechargeable batteries of different electro-chemical designs, the exact curve is different for different battery types and additionally shows some battery-to-battery variation.

It can be seen that in an initial phase I, the voltage drop over time is rather large, followed by a long phase II, where the voltage curve is almost horizontal, (e.g., the voltage drop per time is small). As the battery approaches the end of its useful lifetime in phase III, there is a steep voltage drop per time.

In accordance with the disclosure, the time interval between two consecutive tests is not constant. In the initial phase I, where the battery voltage is high, a comparatively long testing interval between consecutive tests is sufficient. In the main operation phase II, the testing interval is reduced. In the end phase III with a steep drop of the voltage over time, it is further reduced in order to ensure early detection of the end of the battery lifetime.

With $T_1$, $T_2$, $T_3$ being interval lengths and U1, U2 being threshold voltage levels for switching the testing intervals, the testing interval T is determined as $$T=T_1 \text{ for } U \geq U_1$$

$$T=T_2 \text{ for } U_1 > U \geq U_2$$

$$T=T_3 \text{ for } U < U_2. \quad (2)$$

For an Alkaline cell of 1.5V nominal voltage, the interval lengths may, for example be chosen as $T_1$=30 min, $T_2$=10 min, $T_3$=1 min. The threshold voltage levels may be chosen as $U_1$=1.3 V, $U_2$=1.2 V. The threshold voltage levels are favorably selected such that they approximately correspond to the transition from phase I to phase II and from phase II to phase III for a typical and non-defective battery. The control unit 112 evaluates the terminal voltage U with the resistance 116 being connected to the battery 100 and modifies the testing interval according to equations (2).

Besides the threshold levels for switching the testing interval, the control unit 112 compares the terminal voltage with at least one alerting voltage threshold and triggers a user alert if the terminal voltage falls below the alerting voltage threshold. The alerting voltage threshold is favorably selected somewhat above a minimum terminal voltage which is required for safe operation of the device. As an example, the alerting voltage threshold may be 0.8 V. If the terminal voltage drops below the alerting voltage threshold, the battery has to be replaced soon. As a favorable option, the terminal voltage may further be compared to a pre-alerting voltage threshold which is somewhat higher than the alerting voltage threshold. A pre-alert is triggered if the terminal voltage falls below the pre-alerting voltage threshold. This gives the user some additional time for replacing the battery while the device is still fully operable. The pre-alerting voltage threshold is favorably selected such that the device can be safely operated for some further hours following the terminal voltage dropping below the pre-alerting voltage threshold.

It should be noted that the number of three discrete interval lengths and two corresponding threshold voltage levels for switching between these testing intervals is exemplarily. In some embodiments, a different number of k testing intervals, in particular a larger number, and k−1 corresponding threshold voltage levels may be used as well. Furthermore, the testing interval may be modified in a substantially continuous way. The testing interval may, for example, be selected as $$T=T_1 \text{ for } U \geq U_1$$

$$T=T_1+k*(U-U_1) \text{ for } U_1 > U \geq U_2$$

$$T=T_3 \text{ for } U < U_2. \quad (3)$$

For this type of embodiment, the testing interval T decreases linearly with the terminal voltage between $T_1$ as maximum interval and $T_3$ as minimum with slope $k=(T_3-T_1)/(U_2-U_1)$.

Alternatively or additionally to the absolute voltage U, the derivative dU/dt or an approximation of dU/dt may be numerically calculated by the testing unit 110 and may used as control variable. In such an embodiment, the testing interval is modified for the first time where the absolute value of the derivative decreases and assumes a value close to zero, e.g., at the transition from phase I to phase II and is modified for the second time as the absolute value for the derivative start to considerably increase, e.g., at the transition from phase II to phase III. Changing between discrete testing intervals may be carried out in a way analogous to (2). A continuous modification may be carried out in way analogous to (3), but replacing U by dU/dt as control variable.

Figure 4:
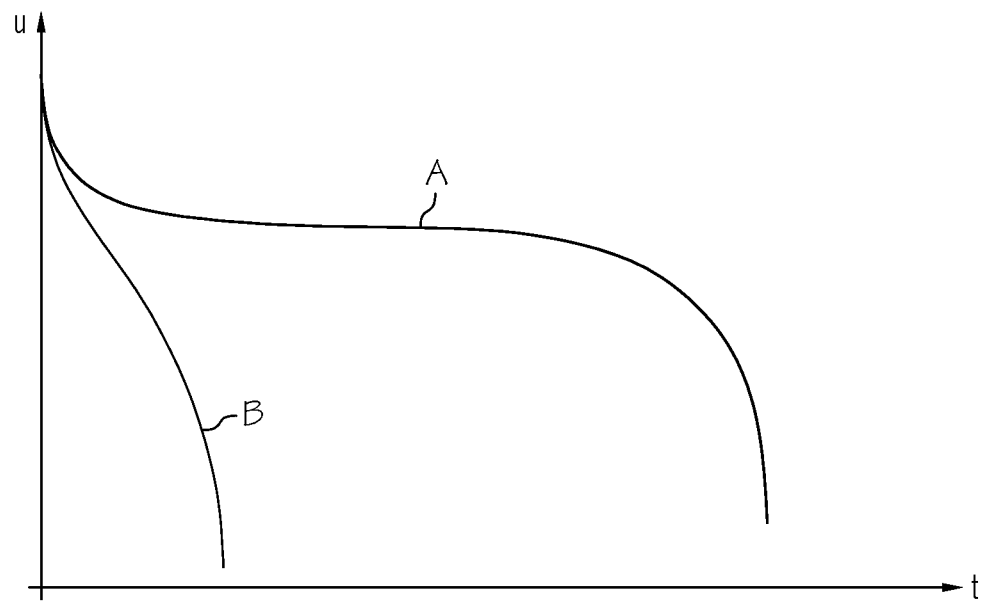
FIG. 4 shows the terminal voltage of two different batteries as a function of time.

In a further embodiment, the second time derivative of the terminal voltage serves as a control variable. The second time derivative is favorable in so far as it reflects changes in the terminal voltage, and in particular the change between the phases I, II and II as shown in FIG. 4 as compared to the terminal voltage itself or its first time derivative.

The testing interval may be determined in dependence of the terminal voltage or its time derivative according to further functions. It may, for example, decrease linearly or non-linearly with the terminal voltage without providing a fixed upper and/or lower limit as it is the case in (3).

Since the off-current voltage curve and the internal resistance curve (see FIG. 9) are dependent on the battery type and in particular its electro-chemical design, some or all parameters may be selected in dependence of the battery type. The device may allow the user to choose between different battery types and set the parameters in dependence of the selection.

Additionally, the device 10 disclosed herein has the advantage that the battery is tested sufficiently often to detect when it should be replaced without unnecessarily reducing its lifetime through unrequired tests. Therefore, the battery 100 is used more efficiently.

A further favorable characteristic of the exemplary device 10 can be seen from FIG. 4. FIG. 4 schematically shows the terminal voltage of two batteries "A" and "B" over time. For battery "A", the curve corresponds to the one shown in FIG. 2. Battery "B", in contrast, is a defective battery. While the initial terminal voltage is as expected, it drops fast and steeply under load. This may occur in a time span of typically a few hours after inserting the battery into the device. For an existing device with a testing interval of, e.g., 3 min, the voltage may drop below a pre-alerting voltage threshold, the alerting voltage threshold and below the minimum voltage required for the device operation so fast that the device terminates operation without any warning or alert. In a device according to this disclosure, this can prevented due to the testing interval being reduced as the voltage drops such that the testing interval is sufficiently short to detect the steep voltage decrease prior to the voltage dropping below the minimum operating voltage and in particular below the voltage required for generating a user alert.

In the following, reference is made to FIG. 5, FIG. 6, and FIG. 10, which illustrate a further exemplary embodiment. FIG. 5 shows a schematic electrical diagram of a device 10 with a design and operation similar to the previously described embodiment. The design and the operation of the testing unit 310, however, are somewhat different as compared to the previously described embodiments.

Instead of a single test load, two resistors 316, 317 with different test load resistances $R_1$ and $R_2$, are provided as alternative test loads. Accordingly, the control unit 312 and the switch 318 are designed such that alternatively none or either of the resistors 316, 317 can be coupled to the battery 100. For carrying out a test, the control unit 312 controls the switch 318 to couple the resistors 316, 317 to the battery 100 in consecutive order and controls the measurement unit 114 to measure the corresponding terminal voltage $U_1$ and $U_2$.

FIG. 6 shows the curve 200 of the terminal voltage U and shows, in addition, a second curve 210 which represents the difference voltage $\Delta U = |U_2 - U_1|$. The difference voltage is correlated with the internal resistance $R_i$ of the battery 100. Assuming the internal resistance $R_i$ to be zero, the terminal voltage U as measured by the measurement unit 114 would be substantially identical in both cases and be substantially identical to the open-circuit voltage $U_0$, meaning the difference voltage $\Delta U$ would be approximately zero. For a non-zero internal resistance, the voltage drop over the internal resistor 104 is proportional to the current that is drawn from the battery 100.

FIG. 10 illustrates exemplary curves of the terminal voltage of the battery 100, with curve 610 being representative of a fresh or fully charged battery; curve 610' being representative for a partly depleted; and curve 610" for a largely depleted battery. The first portion of the graph, with $t < t_1$, shows the terminal voltage with substantially no current being drawn, such that it approximately equals the off-circuit voltage. For clarifying the effect of stressing the battery 100 with the different test loads, the curves 610, 610', 610" are shown in FIG. 10 with equal off-circuit voltages.

In practice, the off-circuit voltage for the partly depleted battery (curve 610') may be somewhat lower as compared to the fresh battery (curve 610) and still lower for the largely depleted battery (curve 610"); see also FIG. 9. At $t=t_1$, the battery 100 is coupled to resistor 316 of resistance $R_1$, such that a current $I_1$ is drawn. The different resulting terminal voltages are caused by the different internal resistances of the battery 100 as explained above. At $t=t_2$, the battery 100 is coupled to resistor 317 of resistance $R_2$. It is assumed that $R_2$ is smaller than $R_1$, resulting in a larger current, and, thus, a larger voltage drop over the internal resistor of the battery 100 when connected to resistor 317. At $t=t_3$, resistor 317 is disconnected from the battery 100.

In this exemplary embodiment, the difference voltage $\Delta U$ is used as control variable, as indicated by lines 202'. The testing interval is controlled such that the testing interval is long if the difference voltage is small and is short if the difference voltage is high. In some embodiments, a number of (e.g., three) interval lengths is provided and the testing interval is selected as one of these intervals in a substantially analogue way to (2), only replacing the terminal voltage U with the difference voltage $\Delta U$. In some embodiments, the testing interval may be determined in a way analogous to (3) or in a way analogous to any other of the above-described options.

An alert may be triggered if the difference voltage exceeds a given difference voltage threshold and/or if the terminal voltage drops below an alerting voltage threshold as described above. In a further embodiment, the testing interval may be varied based on the internal resistance $R_i$ of the battery 100, with the graph of the internal resistance over time being qualitatively similar to the $\Delta U$ graph (see FIG. 9). The internal resistance $R_i$ of the battery 100 can be determined from the voltages $U_1$, $U_2$ by applying Ohm's law. It may also be determined via further battery impedance measurement circuitry and methods as known in the art. While advanced measurement approaches, such as fuel gauging, require a considerable effort and are not required in many cases, they may be used in some embodiments for accuracy reasons.

In embodiments including measuring the internal resistance of the battery, the device 10 may be designed to trigger an alert based on (1) as given above. The off-circuit voltage $U_0$ which is required for evaluating (1) is determined from the two measured terminal voltages $U_1$ and $U_2$ according to Ohm's law or is determined by the measurement unit 114 if neither of the resistors 316, 317 is coupled to the battery 100 nor further significant current is drawn by the general circuitry 130.

FIG. 7 and FIG. 8, in combination, illustrate a still further exemplary embodiment. The schematic electrical diagram is similar to the one in FIG. 2, but the testing unit 410 is designed and operates somewhat differently. Instead of varying the testing interval, a constant testing interval of, e.g., 3 min, is used in this embodiment, as indicated by lines 202" and the test load resistance R of the test load 416 is altered by the control unit 412. The test load 416 may be implemented as voltage controlled resistor.

FIG. 8 shows the curve 200 of the terminal voltage U in the same way as FIG. 3. In addition, FIG. 8 shows a curve 212 of the test load resistance R as controlled by the control unit 412. The test load resistance may be determined in several ways. In this embodiment, the time derivate dU/dt serves as control variable. The test load resistance may be controlled in dependence of the control variable in various ways. In a favorable embodiment, the test load resistance is controlled to vary linearly with dU/dt between a minimum value and a maximum value in an analogous way to (3). Generally, the test load resistance is controlled to be low if the absolute value of dU/dt is high. The test load resistance is controlled to be high if the absolute value of dU/dt is low; more specifically, if the voltage curve 200 is flat or substantially horizontal. In this way, the test load resistance is reduced at the end of the usage time of the battery. For practical purposes, the derivate dU/dt may be replaced by a numerical approximation, such as a quotient of differences which may be computed from consecutive tests. Similarly, in some embodiments, the second time derivative may be used.

Instead of continuously varying the test load resistance, the test load resistance may be varied in a number of discrete steps as a function of the time derivative of the terminal voltage. In those embodiments, a set of resistors and a set of switches may be provided instead of the variable test load 416. In a further variant, another variable as discussed above serves as control variable. For determining the internal resistance, the variable test load 416 may be controlled to consecutively assume a plurality of different resistances.

FIG. 11 illustrates a still further exemplary embodiment of the present disclosure. This embodiment is different from the previously discussed embodiments in so far as the general circuitry 530 is not powered by the battery 100 directly but via a voltage converter 525. The voltage converter 525 is typically a DC/DC step-up converter that provides a constant output voltage $U_2$ for an input voltage being in a given range, with $U_2 > U$. Such converters are commercially available and are favorable if the required operation voltage of the general circuitry 530 is, at least in part, higher than the battery voltage. In an exemplary device, the battery 100 may have a nominal voltage of 1.5V while the general circuitry 530, and in particular the actuator of the dosing unit, require a higher operation voltage, such as 3V, 5V, 6V or even higher.

The voltage converter 525 transforms a voltage U and a current I on the input side to a voltage $U_2$ and a current $I_2$ on its output side such that $$U_2 * I_2 = k * U * I, \quad (4a)$$

$$P_2 = k * P, \quad (4b).$$

In (4), $P_2$ is the output power of the voltage converter 525 may be the power drawn by the general circuitry 530; P is the input power of the voltage converter 525 and may be embodied as the power drawn from the battery 100; and k<1 is the converter efficiency.

The output voltage $U_2$ of the voltage converter 525 is controlled by the voltage converter 525 to be constant, such that the output current $I_2$ is given by the power consumption $P_2$ of the general circuitry 530. Accordingly, the output current $I_2$ assumes a maximum $I_{max}$ when this power assumes a maximum value $P_{2,max}$.

With the product U*I being defined by (4), the resulting current I drawn from the battery 100 for a given power P is dependent on its off-circuit voltage $U_0$ and its internal resistance $R_i$. If the off-circuit voltage $U_0$ is high and the internal resistance $R_i$ is low, the current I is low. With an increasing internal resistance $R_i$ and/or a decreasing off-current voltage $U_0$, the current I increases accordingly.

For the voltage converter 525 and, thus, the device 10, to operate as intended, the voltage on the input side of the voltage converter 525 must not fall below a minimum operating voltage $U_{min}$. That is, the condition $$U \geq U_{min} \quad (5)$$

must be met.

In the embodiment illustrated in FIG. 11, the testing unit 510 includes a control unit 512 and a measurement unit 520, the measurement unit 520 including a voltage measurement unit as well as a resistance and/or impedance measurement unit. The measurement unit allows determining both the off-circuit voltage $U_0$ and the internal resistance $R_i$ of the battery 100. The measurement unit 520 may comprise an arrangement with at least two resistors as illustrated in FIG. 5 or another battery impedance measurement circuitry as known in the art.

By applying (4) and the additional relation $$U = U_0 - R_i * I, \quad (6),$$

for the terminal voltage U, a quadratic equation for the terminal voltage U, and, thus, the voltage on the input side of the voltage converter 525 can be determined for given $U_0$, $R^i$, $P_2$ and k. The quadratic equation may be solved by the control unit 512 analytically or numerically using an approach according to the state of the art. For being capable for powering the device, the battery 100 must meet the condition (5) for $P_2 = P_{2,max}$.

In addition, it will be understood that for a battery having an internal resistance the power $P_{max}$ that can be drawn from the battery has an absolute upper limit which is given if the load resistance powered by the battery, e.g., the quotient of terminal voltage and current drawn from the battery, equals the internal resistance. Since the internal resistance increases with the battery being depleted, the maximum power that can be drawn from the battery is reduced. For being capable of powering the device, the power drawn by the voltage converter 525 must not exceed the maximum power that can be drawn from the battery, that is, $$P \leq P_{max} \quad (7).$$

In each test, the testing unit 510 carries out the steps of determining the off-current voltage $U_0$ and the internal resistance $R_i$ of the battery 100 and determines if the conditions (5, 7) are met for $P_2 = P_{2,max}$. An alert is triggered if either of these condition is not met.

Alternative to the maximum power $P_{2,max}$, another reference power may be used as discussed above. For safety purposes and in order to provide a time span in which the battery 100 may be replaced with the device 10 still operating, the terminal voltage U may be tested against an alerting threshold voltage that is somewhat higher as compared to the minimum operating voltage $U_{min}$. In this embodiment, each individual battery 100 is largely exploited.

The testing may be varied according to either of the methods as discussed above and any of the previously discussed control variables may be used. Alternatively or additionally, the difference between the terminal voltage U and the minimum operating voltage $U_{min}$ of the voltage converter may serve as control variable.

It should be noted that the approach as described with reference to FIG. 11 may in an analogous way be applied for a device that is not powered by a voltage converter but draws a constant or substantially constant power over a large range of the terminal voltage of the energy storage. In this case, (4) holds true with $U_2 = U$, and, thus $P_2 = P$ with a converter efficiency of k=1.

FIG. 12 shows a flowchart illustrating an embodiment of a process, in accordance with the present disclosure. As illustrated in block 750, tests may be repeatedly carried out during operation of the ambulatory infusion device 10. At least one of the tests may include a determination of a control variable. The control variable may be indicative of a capability of the electrical energy storage for further powering the ambulatory infusion device 10. At block 752, the testing can be varied in dependence of the control variable. At block 754, a determination can be made regarding whether the input voltage falls below a minimum operating voltage. In response to a determination that the input voltage falls below the minimum operating voltage, a alert may be generated.

The invention claimed is:

1. Ambulatory infusion device, comprising:
   an energy storage for storing electrical energy utilized for powering the ambulatory infusion device, the energy storage serving as a primary power source of the ambulatory infusion device, the energy storage being successively depleted during application;
   a dosing unit with an electrically powered actuator and an electronic controller, the electronic controller controlling operation of the electrically powered actuator; and
   a testing unit for testing the energy storage, the testing unit configured to repeatedly carry out a test during operation of the ambulatory infusion device, the test including determining a control variable, the control variable being indicative of a capability of the energy storage for further powering the ambulatory infusion device,
   wherein the testing unit is configured to vary the testing of the energy storage in dependence of the control variable.

2. The ambulatory infusion device according to claim 1, wherein the testing unit is configured to vary the testing by reduce a testing interval for carrying out consecutive tests as a change of the control variable indicates a decreasing capability of the energy storage for further powering the ambulatory infusion device.

3. The ambulatory infusion device according to claim 1, wherein the testing unit comprises a test load having a test load resistance, wherein the test includes connecting the test load to the energy storage and the testing unit is configured to vary the testing by reducing the test load resistance as a change of the control variable indicates a decreasing capability of the energy storage for further powering the ambulatory infusion device.

4. The ambulatory infusion device according to claim 1, wherein the control variable includes at least one of the following: a terminal voltage of the energy storage, an internal resistance of the energy storage, a first variable derived from the terminal voltage, and a second variable derived from the internal resistance.

5. The ambulatory infusion device according to claim 2, wherein the testing unit is configured to reduce the testing interval upon at least one of the following: a decreasing terminal voltage and an increasing internal resistance.

6. The ambulatory infusion device according to claim 3, wherein the testing unit is configured to reduce the test load resistance upon at least one of the following: a decreasing terminal voltage and an increasing internal resistance.

7. The ambulatory infusion device according to claim 1, wherein the testing unit is configured to trigger an alert upon the test indicating a lack of capability of the energy storage to further power the ambulatory infusion device.

8. The ambulatory infusion device according to claim 1, wherein the ambulatory infusion device is at least partially powered by a voltage converter and wherein the testing unit is configured to trigger an alert upon the test indicating an input voltage of the voltage converter falling below a minimum operating voltage of the voltage converter.

9. A method for testing an electrical energy storage of an ambulatory infusion device, the electrical energy storage serving as a primary power source of the ambulatory infusion device, the electrical energy storage being successively depleted during application, the method comprising:
   repeatedly carrying out tests during operation of the ambulatory infusion device, at least one of the tests including a determination of a control variable, the control variable being indicative of a capability of the electrical energy storage for further powering the ambulatory infusion device; and
   varying the testing in dependence of the control variable.

10. The method according to claim 9, further comprising varying the at least one test by reducing a testing interval for carrying out consecutive tests as a change of the control variable that indicates a decreasing capability of the electrical energy storage for further powering the ambulatory infusion device.

11. The method according to claim 9, further comprising coupling a test load to the electrical energy storage, the test load having a test load resistance and wherein varying the testing comprises reducing the test load resistance as a change of the control variable that indicates a decreasing capability of the electrical energy storage for further powering the ambulatory infusion device.

12. The method according to claim 9, further comprising determining at least one of the following: a terminal voltage of the electrical energy storage, an internal resistance of the electrical energy storage, a variable derived from the terminal voltage, and the internal resistance as the control variable.

13. The method according to claim 10, further comprising reducing the testing interval for carrying out consecutive tests upon at least one of the following: a decreasing terminal voltage and an increasing internal resistance.

14. The method according to claim 9, further comprising triggering an alert upon a test indicating a lack of capability of the electrical energy storage for further powering the ambulatory infusion device.

15. The method according to claim 9, further comprising triggering an alert upon a test indicating that the input voltage of a voltage converter falling below a minimum operating voltage of the voltage converter, wherein the ambulatory infusion device is powered, at least in part, by the voltage converter.

* * * * *

UNITED STATES PATENT AND TRADEMARK OFFICE
CERTIFICATE OF CORRECTION

PATENT NO. : 8,476,868 B2  
APPLICATION NO. : 12/977392  
DATED : July 2, 2013  
INVENTOR(S) : Thomas Rufer et al.

Page 1 of 1

It is certified that error appears in the above-identified patent and that said Letters Patent is hereby corrected as shown below:

In the Specifications

Col. 1, Line 19, "Infusion." should read --Infusion).--;

Col. 3, Line 32, "drawn form at a" should read --drawn from at a--;

Col. 4, Line 25, "a control variables" should read --a control variable--;

Col. 5, Lines 39-40, "may be generally be performed" should read --may be generally performed--;

Col. 8, Line 32, "devises" should read --devices--;

Col. 9, Line 55, "U1, U2" should read --U1, U2--;

Col. 10, Line 46, "and may used" should read --and may be used--;

Col. 10, Line 55, "carried out in way" should read --carried out in a way--;

Col. 10, Line 61, "phases I, II and II" should read --phases I, II and III--;

Col. 11, Line 26, "this can prevented due" should read --this can be prevented due--;

Col. 11, Line 63, "for a partly depleted;" should read --for a partly depleted battery--;

Col. 13, Lines 43-44, "525 may be the" should read --525 and may be the--;

Col. 14, Line 16, "$R^i$" should read --$R_i$--;

Col. 14, Line 39, "if either of these condition is" should read --if either of these conditions is--;

Col. 15, Line 6, "a alert" should read --an alert--; and

In the Claims  
Col. 15, Claim 2, Line 27, "by reduce" should read --by reducing--.

Signed and Sealed this  
Fifteenth Day of April, 2014

Michelle K. Lee  
*Deputy Director of the United States Patent and Trademark Office*

UNITED STATES PATENT AND TRADEMARK OFFICE
CERTIFICATE OF CORRECTION

Page 1 of 2

PATENT NO. : 8,476,868 B2
APPLICATION NO. : 12/977392
DATED : July 2, 2013
INVENTOR(S) : Thomas Rufer et al.

It is certified that error appears in the above-identified patent and that said Letters Patent is hereby corrected as shown below:

In the Specifications

Col. 1, Line 19, "Infusion." should read --Infusion).--;

Col. 3, Line 32, "drawn form at a" should read --drawn from at a--;

Col. 4, Line 25, "a control variables" should read --a control variable--;

Col. 5, Lines 39-40, "may be generally be performed" should read --may be generally performed--;

Col. 8, Line 32, "devises" should read --devices--;

Col. 9, Line 55, "U1, U2" should read --$U_1$, $U_2$--;

Col. 10, Line 46, "and may used" should read --and may be used--;

Col. 10, Line 55, "carried out in way" should read --carried out in a way--;

Col. 10, Line 61, "phases I, II and II" should read --phases I, II and III--;

Col. 11, Line 26, "this can prevented due" should read --this can be prevented due--;

Col. 11, Line 63, "for a partly depleted;" should read --for a partly depleted battery--;

Col. 13, Lines 43-44, "525 may be the" should read --525 and may be the--;

Col. 14, Line 16, "$R^i$" should read --$R_i$--;

Col. 14, Line 39, "if either of these condition is" should read --if either of these conditions is--;

Col. 15, Line 6, "a alert" should read --an alert--; and

This certificate supersedes the Certificate of Correction issued April 15, 2014.

Signed and Sealed this
Twentieth Day of May, 2014

Michelle K. Lee
*Deputy Director of the United States Patent and Trademark Office*

CERTIFICATE OF CORRECTION (continued)
U.S. Pat. No. 8,476,868 B2

In the Claims

Col. 15, Claim 2, Line 27, "by reduce" should read --by reducing--.